(12) United States Patent
Kerppola

(10) Patent No.: US 7,588,907 B2
(45) Date of Patent: Sep. 15, 2009

(54) UBIQUITIN MEDIATED FLUORESCENCE COMPLEMENTATION ASSAY

(75) Inventor: Tom Kerppola, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 44 days.

(21) Appl. No.: 11/445,612

(22) Filed: Jun. 2, 2006

(65) Prior Publication Data
US 2007/0059731 A1  Mar. 15, 2007

Related U.S. Application Data

(60) Provisional application No. 60/686,557, filed on Jun. 2, 2005.

(51) Int. Cl.
*G01N 33/53* (2006.01)
*C07K 14/00* (2006.01)
(52) U.S. Cl. .................. 435/7.8; 435/69.7; 530/402
(58) Field of Classification Search .................. None
See application file for complete search history.

(56) References Cited

U.S. PATENT DOCUMENTS

| 6,140,132 A | 10/2000 | Tsien |
| 6,150,176 A | 11/2000 | Tsien |
| 6,316,223 B1 | 11/2001 | Luo et al. |

OTHER PUBLICATIONS

Luker and Piwnica-Worms, "Optimizing Luciferase Protein Fragment Complementation for Bioluminescent Imaging of Protein-Protein Interactions in Live Cells and Animals", Methods in Enzymology 385: 349-360 (2004).*
Nyfeler et al., "Capturing protein interactions in the secretory pathway of living cells", PNAS 102(18): 6350-6355 May 2005.*
Goldknopf et al., "Chromatin Cojugate protein A24 Is Cleaved and Ubiquitin Is Lost During Chicken Erthropoiesis" (1980) J. Biol. Chem. 255, 10555-10558.
Pickart, "Back to the Future with Ubiquitin" (2004) Cell 116, 181-190.
McGuire et al., supra "ATP-Stimulated Proteolysis in Soluab;e Extracts of BHK 21/C13 Cells" (1988) Arch. Biochem. Biophys. 262, 273-285.
Driscoll et al., "The Proteasome (Multicatalytic Protease) Is a Component of the 1500-kDa Proteolytic Complex Which Degrades Ubiquitin-congugated Proteins" (1990) J. Biol. Chem. 265, 4789-4792.
Hicke and Riezman, "Ubiquitination of a Yeast Plasma Membrane Receptor Signals Its Ligand-Stimulated Endocytosis" (1996) Cell 84, 277-287.
Babst et al., "Mammalian Tumor Susceptibility gene 101 (TSG101) and the Yeast Homologue, Vps23p, Both Function in Late Endosomal Traficking" (2000) Traffic 1, 248-258.
Kumar et al., "Cloning of a cDNA Which Encodes a Novel Ubiquitin-like Protein" (1993) Biochem. Biophys. Res. Commun. 195, 393-399 (1997) Cell 88:97-107.

Schwartz et al., A Superfamily of Protein tags:ubiquitin, SUMO and related modifiers. (2003) Trends Biochem. Sci. 28, 321-328.
Salghetti et al., "Regulation of Transcriptional Activation Domain Function by Ubiquitin" (2001) Science 293, 1651-1653.
Fang et al., "Dysregulation of T lymphocyte function in itchy mice: a role for itch in TH2 Differentiation" (2002) Nat. Immunol. 3, 281-287.
Kaiser et al., "Regulation of Transcription by Ubiquitination without proteolysis: Cdc34/SCFmet30-Medicated Inactivation of the Transcription Factor Met4" (2000) Cell 102, 303-314.
Muller et al., "Conjugation with the ubiquitin-related modifier SUMO-1 regulated the partitioning of PML within the nucleus" (1998) EMBO J. 17, 61-70.
Ross et al., "SUMO-1 maodification Represses Sp3 Transcriptional Activation and modulates Its Subnuclear Localization" (2002) Mol. Cell 10, 831-842.
Fogal et al., Regulation of p53 Activity in Nuclear Bodies by a specific PML Isoform(2000) EMBO J. 19, 6185-6195.
Rodriguez et al., SUMO-1 Modification Activates the Transcriptional Response of p53(1999) EMBO J. 18, 6455-6461.
Vogt, "Fortuitous Convergences: the beginings of JUN" (2002) Nat. Rev. Cancer 2, 465-469.
Treier et al., Ubiquitin-Dependent c-Jun Degradation In Vivo Is Mediated by the δ Domain(1994) Cell 78, 787-798.
Musti et al., Reduced Ubiquitin-Dependent Degradation od c-Jun After Phosphorylation by MAP Kinases (1997) Science 275, 400-402.
Wertz et al., ("Human De-Etiolated-1 regulated c-Jun by Assembling a CUL4A Ubiquitin Ligase"2004) Science 303, 1371-1374.
Nateri et al., "The Ubiquitin Ligase SCF antagonizes Apoptotic JNK Signaling" (2004) Science 303, 1374-1378.
Barila et al., "A nuclear tyrosine Phosphorylation circuit:c-Jun as an acyivator and substrate of c-Abi and JNK"(2000) EMBO J. 19, 273-281.
Prasher et al., "Primary Structure of the Aequorea victoria green-florescent protein" (1992), Gene, 111:229-233.
Chalfie et al., "Green Fluorescent protein as a Marker for gene Expression" 1994, Science, 263:802-805.
Ormo et al., "Crystal structure of the Aequorea vistoria Green Fluorescent Protein" 1996, Science 273, 1392.
Yang et al., "The Molecular Structure of green fluorescent protein"1996 Nature Biotechnol. 14, 1246.
Cody et al., "Chemical Structure of the Hexapeptide Chromophere of the Aequorea Green-fluorescent Protein" 1993, Biochemistry 32:1212-1218.
Haas et al., "Codon Usage Limitation in the expression of HIV-1 envelope glycoprotein" Curr. Biol. 6:315-324 (1996).
Crameri et al., "Improved green Fluorescent Protein by Molecular Evolution Using DNA Shuffling" Nature Biotechnol. 14:315-319 (1996).
Angers et al., "The HECT Domain Ligase Itch Ubiquitinates Endophilin and Localizes to the trans-Golgi Network and Endosomal System"(2004) J. Biol. Chem. 279, 11471-11479.

(Continued)

*Primary Examiner*—Anand U Desai
(74) *Attorney, Agent, or Firm*—Casimir Jones, S.C.

(57) ABSTRACT

The present invention relates to methods and compositions for identifying covalent joining or modification of proteins. In particular, the present invention relates to covalent fluorescence complementation assays for the detection of modified (e.g., ubiquitinated) proteins. The present invention further relates to the use of such fluorescence complementation assays in drug screening and research applications.

8 Claims, 14 Drawing Sheets

OTHER PUBLICATIONS

Hu et al., "Visualization of Interactions among bZIP and Rel family Proteins in Living Cells Using Bimolecular Fluorescence Complementation" (2002) Mol. Cell 9, 789-798.

Conaway et al., Emerging Roles of Ubiquitin in Transcription Regulation (2002) Science 296, 1254-1258.

von der Lehr et al., "The F-Box Protein Skp2 Participates in c-Myc Protrosomal degradation and Acts as a Cofactor for c-Myc-Regulated Transcriptoio" (2003) Mol. Cell 11, 1189-1200.

Seeler and Dejean, A. "Nuclear and Unclear Functions of SUMO" (2003) Nat. Rev. Mol. Cell. Biol. 4, 690-699.

Hu et al., "Simultaneous visualization of multiple protein interactions in living cells using multicolor fluorescence complementation analysis" (2003) Nat. Biotechnol. 21, 539-545.

Chen et al., "Identification of Two Lysosomal Membrane Glycoproteins" (1985) J. Cell Biol. 101, 85-95.

Tisdale et al., "GTP-Binding Mutants of Rab1 and Rab2 are Potent Inhibitors of Vesicular Transport from the Endoplasmic reticulum to the Golgi Complex" (1992) J. Cell Biol. 119, 749-761.

Keystone Symposium on Ubiquitin and Signaling, "Visualization of Ubiquitin-Family Conjugates in Living Cells ny Ubiquitin-Mediated Fluorescence Complementation" Taos, NM, Feb. 2005.

Advances in Nanogenomics, "Visualization of Protein Interactions and Modifications in Living Cells" The Jackson Laboratory, Bar Harbor, ME, Sep. 2004.

Société de Biologie Cellulaire de France: Imaging the Cell, "Visualization of Protein Interactions and Modification in Living Cells" Montpellier, France, Jun. 2004.

Microscopy Society of American Meeting, "Imaging Protein Interactions and Modifications Living Cells" Savannah, GA, Aug. 2004.

16th International Institute of Genetics and Biophysics Workshop, "Visualization of Protein Interactions and Modifications in Living Cells" Capri, Italy, Oct. 2003.

EMBO Workshop on Advanced Light Microscopy—"Visualization of Protein Interactions and Modifications in Living Cells using Biomecular fluorescence Complementation Analysis" ELMI, Gothenburg, Sweden, May 2004.

Cold Spring Harbor Meeting on Nuclear Structure and Dynamics, "Visualization of Ubiquitin-Family Conjugates in Living Cells ny Ubiquitin-Mediated Fluorescence Complementation" NY, Sep. 2004.

Cold Spring Harbor Meeting on Neuronal Imaging, "Visualization of Protein Interactions and Modifications in Living Cells using Biomecular Fluorescence Complementation Analysis" Cold Spring Harbor, NY, Mar. 2005.

Mahajan et al., "A Small Ubiquitin-Related Polypeptide Involved in targeting RanGAP1 to Nuclear Pore Complex Protein RanBP2" (1997)Cell 88, 97-107.

* cited by examiner

Figure 7
SEQ ID NO: 2

MVSKGEELFTGVVPILVELDGDVNGHKFSVSGEGEGDATYGKLTLKFICTTGKLPVPWPTLVTTFGYGLQC
FARYPDHMKQHDFFKSAMPEGYVQERTIFFKDDGNYKTRAEVKFEGDTLVNRIELKGIDFKEDGNILGHKL
EYNYNSHNVYIMA

Figure 8
SEQ ID NO: 3

DKQKNGIKVNFKIRHNIEDGSVQLADHYQQNTPIGDGPVLLPDNHYLSYQSALSKDPNEKRDHMVLLEFVT
AAGITLGMDELYK

Figure 9
SEQ ID NO: 4

MVSKGEELFTGVVPILVELDGDVNGHKFSVSGEGEGDATYGKLTLKFICTTGKLPVPWPTLVTTFGYGLQC
FARYPDHMKQHDFFKSAMPEGYVQERTIFFKDDGNYKTRAEVKFEGDTLVNRIELKGIDFKEDGNILGHKL
EYNYNSHNVYIMADKQKNGIKVNFKIRHNIE

Figure 10
SEQ ID NO: 5

DGSVQLADHYQQNTPIGDGPVLLPDNHYLSYQSALSKDPNEKRDHMVLLEFVTAAGITLGMDELYK

Figure 11
SEQ ID NO:6

MVSKGEELFTGVVPILVELDGDVNGHKFSVSGEGEGDATYGKLTLKFICTTGKLP
VPWPTLVTTLTWGVQCFSRYPDHMKQHDFFKSAMPEGYVQERTIFFKDDGNYK
TRAEVKFEGDTLVNRIELKGIDFKEDGNILGHKLEYNYISHNVYITADKQKNGIK
ANFKIRHNIE

Figure 12
SEQ ID NO:8

MvSKGEELFTGVVPILVELDGDVNGHKFSVSGEGEGDATYGKLTLKFICTTGKLP
VPWPTLVTTltYGVQCFSRYPDHMKQHDFFKSAMPEGYVQERTIFFKDDGNYKT
RAEVKFEGDTLVNRIELKGIDFKEDGNILGHKLEYNYNSHNVYIMADKQKNGIK
VNFKIRHNIE

Figure 13
SEQ ID NO:8

MVSKGEELFTGVVPILVELDGDVNGHKFSVSGEGEGDATYGKLTLKFICTTGKLPVPWPTLVTTFGYGLMC
FARYPDHMKQHDFFKSAMPEGYVQERTIFFKDDGNYKTRAEVKFEGDTLVNRIELKGIDFKEDGNILGHKL
EYNYNSHNVYIMADKQKNGIKVNFKIRHNIE

Figure 14

VN1-154 (SEQ ID NO:9):
MVSKGEELFTGVVPILVELDGDVNGHKFSVSGEGEGDATYGKLTLKLICTTGKLP
VPWPTLVTTLGYGLQCFARYPDHMKQHDFFKSAMPEGYVQERTIFFKDDGNYK
TRAEVKFEGDTLVNRIELKGIDFKEDGNILGHKLEYNYNSHNVYITAD

VN1-172 (SEQ ID NO:10):
MVSKGEELFTGVVPILVELDGDVNGHKFSVSGEGEGDATYGKLTLKLICTTGKLP
VPWPTLVTTLGYGLQCFARYPDHMKQHDFFKSAMPEGYVQERTIFFKDDGNYK
TRAEVKFEGDTLVNRIELKGIDFKEDGNILGHKLEYNYNSHNVYITADKQKNGIK
ANFKIRHNIEANSSIDLISVPVEYPYDVPDYASRMQIFVKTLTGKTITLEVESSDTI
DNVKSKIQDKEGIPPDQQRLIFAGKQLEDGRTLSDYNIQKESTLHLVLRLRGG

VC155-238 (SEQ ID NO:11):
ADKQKNGIKANFKIRHNIEDGGVQLADHYQQNTPIGDGPVLLPDNHYLSYQSAL
SKDPNEKRDHMVLLEFVTAAGITLGMDELYK

US 7,588,907 B2

UBIQUITIN MEDIATED FLUORESCENCE COMPLEMENTATION ASSAY

This application claims priority to U.S. Provisional Application Ser. No. 60/686,557, filed Jun. 2, 2005, the disclosure of which is herein incorporated by reference in its entirety.

FIELD OF THE INVENTION

The present invention relates to methods and compositions for identifying covalent joining or modification of proteins. In particular, the present invention relates to covalent fluorescence conjugation with fluorescence complementation assays for the detection of modified (e.g., ubiquitinated) proteins. The present invention further relates to the use of such fluorescence complementation assays in drug screening and research applications.

BACKGROUND OF THE INVENTION

Covalent modification of proteins is a common mechanism for alteration of protein function and stability. The small peptide ubiquitin is covalently linked to lysine residues on many proteins. Ubiquitination often targets proteins for degradation. The ubiquitin-proteasome system is responsible for quality control and regulatory functions in the cell.

Existing methods for the detection of ubiquitination in a cell rely on donor-acceptor methods such as fluorescence resonance energy transfer and time-resolved fluorescence. Such methods are cumbersome and subject to interference by cellular components.

What is needed are simple, robust methods for detecting covalent protein conjugations in a variety of situations.

SUMMARY OF THE INVENTION

The present invention relates to methods and compositions for identifying covalent joining or modification of proteins. In particular, the present invention relates to covalent fluorescence conjugation with fluorescence complementation assays for the detection of modified (e.g., ubiquitinated) proteins. The present invention further relates to the use of such fluorescence complementation assays in drug screening and research applications.

Accordingly, in some embodiments, the present invention provides covalent fluorescence complementation assays (e.g., ubiquitin-mediated covalent fluorescence assays) for the detection of covalently modified proteins. The methods and compositions of the present invention find use in drug screening (e.g., to screen for drugs that alter ubiquitination or other modifications of proteins) and research (e.g., to identify ubiquitinated proteins and ubiquitination pathways). The methods of the present invention provide the particular advantage of functioning in living cells. Thus, in some embodiments, the methods and compositions of the present invention find use in determining the organ or subcellular location of ubiquitinated proteins.

For example, in some embodiments, the present invention provides a kit for performing a covalent fluorescence complementation assay, comprising: a first vector, the first vector comprising a first nucleic acid sequence encoding a first fragment of a fluorescent protein fused to a gene encoding a first protein (e.g., ubiquitin); and a second vector comprising a second nucleic acid sequence encoding a second fragment of a fluorescent protein operably linked to a nucleic acid comprising an insertion site for the insertion of a protein of interest. In some embodiments, the protein of interest is a protein suspected of being ubiquitinated or otherwise covalently modified. In other embodiments, the protein of interest is known to be covalently modified (e.g., ubiquitinated). In some embodiments, the fluorescent protein comprises a variant of green fluorescent protein. In some embodiments, the first fragment of the fluorescent protein is selected from the group consisting of SEQ ID NOs: 3, 5, 9 and 10. In some embodiments, the second fragment of the fluorescent protein is selected from the group consisting of SEQ ID NOs: 2, 4, 6, 7, 8, and 11. In some embodiments, the kit further comprises a plurality of second nucleic acid sequences encoding the second fragments of a fluorescent protein comprising a plurality of nucleic acid sequences encoding variants of the second fragments, wherein the second fragments are configured for the expression of a plurality of fluorescent fusion proteins configured to emit fluorescence of different wavelengths of light. In some embodiments, the kit further comprises instructions for using the kit for performing covalent fluorescence conjugation assays.

The present invention further provides a method, comprising providing a first fusion protein comprising a first fragment of a fluorescent protein linked to a first protein (e.g., ubiquitin) known to covalently modify a protein of interest; and a second fusion protein comprising a second fragment of the fluorescent protein linked to a protein of interest; and contacting the first and second fragments of the fluorescent protein under conditions such that the first and second fragments of the fluorescent protein associate to form a fluorescent protein complex that generates a optically detectable signal in the presence but not the absence of covalent modification of the protein of interest by the first protein. In some embodiments, the first and second fusion proteins are in a cell. In some embodiments, the cell is in an organism. In some embodiments, the method further comprises the step of detecting the sub-cellular location of the fluorescent signal. In some embodiments, the first fusion protein is encoded by a first vector comprising a first nucleic acid sequence encoding the first fragment of the fluorescent protein and a second nucleic acid sequence encoding the first protein (e.g., ubiquitin) and the second fusion protein is encoded by second vector comprising a third nucleic acid sequence encoding the second fragment of the fluorescent protein and a fourth nucleic acid encoding the protein of interest. In some embodiments, the first fragment of the fluorescent protein is selected from the group consisting of SEQ ID NOs: 3, 5, 9 and 10. In some embodiments, the second fragment of the fluorescent protein is selected from the group consisting of SEQ ID NOs: 2, 4, 6, 7, 8, and 11. In some embodiments, the method further comprises the step of detecting an organ location of the fluorescent signal.

The present invention additionally provides a method of screening compounds, comprising: providing a first fusion protein comprising a first fragment of a fluorescent protein linked to a first protein (e.g., ubiquitin) known to covalently modify a protein of interest; a second fusion protein comprising a second fragment of the fluorescent protein linked to a protein of interest known to be covalently modified by the first protein; and one or more test compounds; and contacting the first and second fragments of the fluorescent protein and the test compound; and detecting the presence or absence of a fluorescent signal. In some embodiments, the fluorescent signal is generated in the presence but not the absence of modification of the protein of interest. In some embodiments, fluorescence signal is altered relative to the fluorescence signal in the absence of the test compound. In some embodiments, the fluorescent signal is decreased in the presence of the test compound. In some embodiments, the decrease in fluorescent signal is due to a decrease in the modification of the protein of interest. In some embodiments, the first and second fusion proteins are in a cell. In some embodiments, the cell is in an organism. In some embodiments, the method further comprises the step of detecting the sub-cellular location of the fluorescent signal. In some embodiments, the first fusion protein is encoded by a first vector comprising a first nucleic acid sequence encoding the first fragment of the fluorescent protein and a second nucleic acid sequence encoding the first protein (e.g., ubiquitin) and the second fusion protein is encoded by second vector comprising a third nucleic acid sequence encoding the second fragment of the fluorescent protein and a fourth nucleic acid encoding the protein of interest. In some embodiments, the first fragment of the fluorescent protein is selected from the group consisting of SEQ ID NOs: 3, 5, 9 and 10. In some embodiments, the second fragment of the fluorescent protein is selected from the group consisting of SEQ ID NOs: 2, 4, 6, 7, 8, and 11. In some embodiments, the method further comprises the step of detecting an organ location of the fluorescent signal.

DESCRIPTION OF THE FIGURES

FIG. 7 shows the amino acid sequence of EYFP(1-154) (SEQ ID NO:2).

FIG. 8 shows the amino acid sequence of EYFP(155-238) (SEQ ID NO:3).

FIG. 9 shows the amino acid sequence of EYFP(1-172) (SEQ ID NO:4).

FIG. 10 shows the amino acid sequence of EYFP(173-238) (SEQ ID NO:5).

FIG. 11 shows the amino acid sequence of ECFP(1-172) (SEQ ID NO: 6).

FIG. 12 shows the amino acid sequence of EGFP(1-172) (SEQ ID NO:7).

FIG. 13 shows the amino acid sequence of Citrine(1-172) (SEQ ID NO:8).

FIG. 14 shows the amino acid sequences of venus protein fragments 1-154 (SEQ ID NO:9); 1-172 (SEQ ID NO:10) and 155-238 (SEQ ID NO:11).

DEFINITIONS

Figure 1:
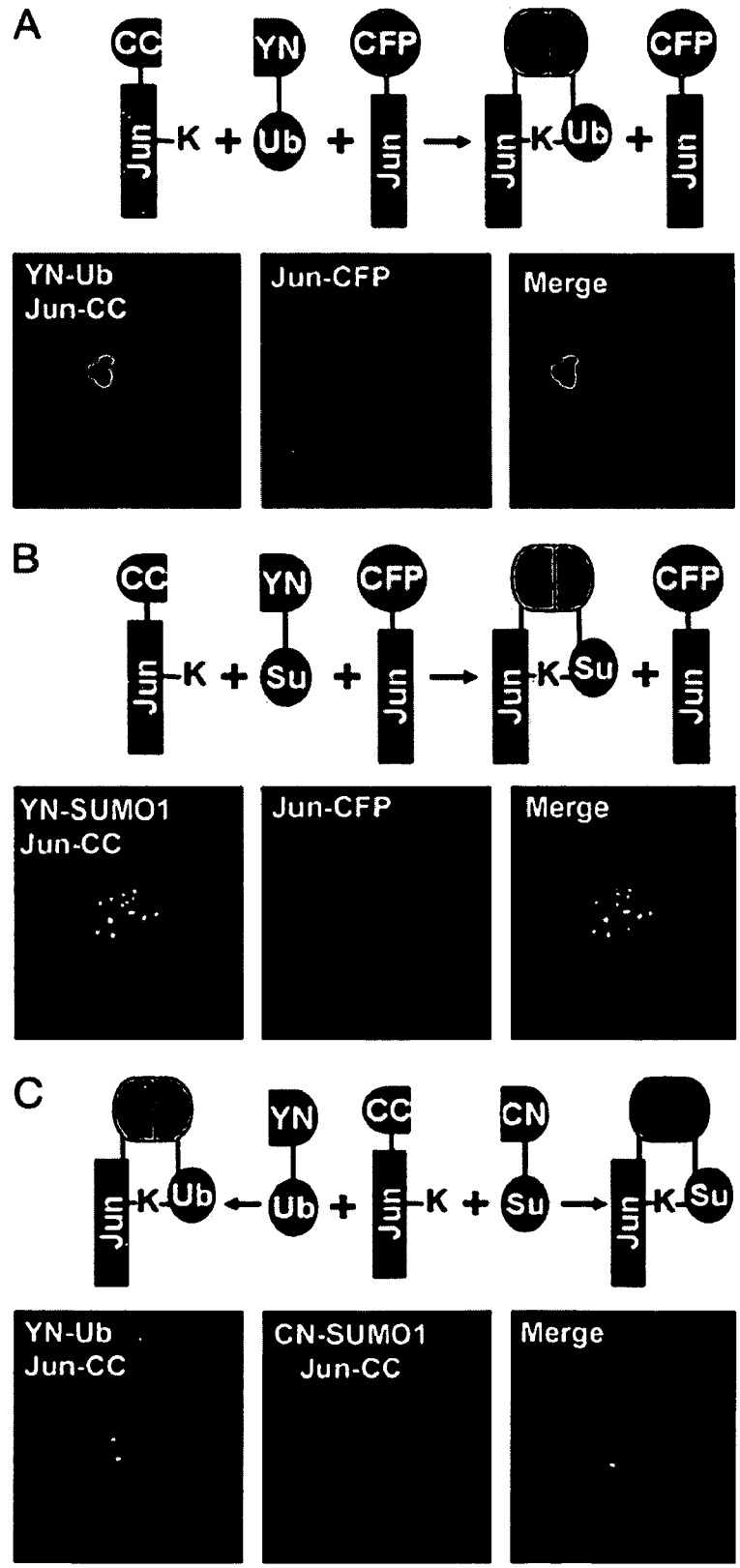
FIG. 1 shows visualization of Jun conjugated to ubiquitin and SUMO1 in living cells. (A) YN-Ub, Jun-CC, and Jun-CFP; (B) YN-SUMO1, Jun-CC, and Jun-CFP; and (C) YN-Ub, CN-SUMO1, and Jun-CC were expressed in COS-1 cells.

To facilitate an understanding of the present invention, a number of terms and phrases are defined below:

As used herein, the term "covalent fluorescence complementation assay" refers to an assay for detecting covalent conjugation between two or more "binding partners" (e.g., polypeptides). For example, in some embodiments, the methods and compositions of the present invention utilize "covalent fluorescence complementation assays," in which two binding partners are used. In some embodiments, each of the binding partners is fused to a fragment of a fluorescent protein. In preferred embodiments, covalent conjugation of the two binding partners results in the association of the two fluorescent protein fragments to generate a fluorescent complex. The generation of the fluorescent conjugate is monitored by observing a fluorescence signal from the conjugate. In preferred embodiments, the fragments of the fluorescent protein do not associate in the absence of a covalent conjugation between the two binding partners.

As used herein, the term "ubiquitin mediated covalent fluorescence complementation assay" refers to a covalent fluorescence conjugation assay in which the covalent modification of a substrate protein by a ubiquitin fused to a first fragment of a fluorescent protein, wherein the substrate protein is fused to a second fragment of a fluorescent protein results in fluorescence signal from the conjugate.

As used herein, the term "conjugation partners" refers to two molecules (e.g., proteins) that are capable of, or suspected of being capable of, forming a covalent conjugate. As used herein, the terms "first conjugation partner" and "second conjugation partner" refer to two conjugation partners that are capable of, or suspected of being capable of, covalently binding with each other.

As used herein, the term "fluorescent protein" refers to any protein that exhibits an intrinsic fluorescent signal. Examples of fluorescent proteins include, but are not limited to, green fluorescent protein, yellow fluorescent protein, citrine fluorescent protein, and blue fluorescent protein. In some preferred embodiments of the present invention, yellow fluorescent protein is utilized.

As used herein, the term "N-terminal fragment of a fluorescent protein" refers to a fragment of a fluorescent protein that encompasses the N-terminus of the protein. Preferred N-terminal fragments are those that are able to re-associate with "C-terminal fragments of a fluorescent protein" to produce fluorescence.

As used herein, the term "C-terminal fragment of a fluorescent protein" refers to a fragment of a fluorescent protein that encompasses the C-terminus of the protein. Preferred C-terminal fragments are those that are able to associate with "N-terminal fragments of a fluorescent protein" to produce fluorescence.

As used herein, the term "kit for performing a covalent fluorescence conjugation assay" (e.g., a ubiquitin mediated covalent fluorescence conjugation assay) refers to a kit comprising materials useful for performing a covalent fluorescence conjugation assay. For example, in some embodiments, the kit includes one or more cloning vectors comprising nucleic acids encoding one or more fragments of a fluorescent protein fused to a cloning region for insertion of a nucleic acid encoding a first protein (e.g., ubiquitin) or candidate for modification protein. In some embodiments, the kits further comprise instructions for performing the assay, as well as any cells, buffer, controls, etc. useful for performing the assay.

As used herein, the term "fusion protein" refers to a single polypeptide chain comprising two or more distinct domains (i.e., two or more segments of proteins or peptides combined in a manner not found in nature; e.g., chimeric proteins, purification tags attached to proteins, etc.). In some embodiments, the domains are present sequentially without any intervening amino acids. In other embodiments, the domains are separated by additional short stretches of amino acid residues (e.g., linkers).

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F (ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of two binding partners means that the interaction is dependent upon the presence of a particular structure (e.g., region) on the proteins; in other words the binding partners are recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of two binding partners refer to an interaction that is not dependent on the presence of a particular structure (e.g., the protein is binding to proteins in general rather that a particular structure).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decreases production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product identical to that found in a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule increase the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA or protein to indicate a level of expression approximately 2-fold higher (or greater) than that observed in a given tissue in a control. Levels of MRNA or protein are measured using any of a number of techniques known to those skilled in the art including, but not limited to Northern blot analysis and quantitative immunofluorescence. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reactions that occur within a natural environment.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to methods and compositions for identifying and characterizing covalent joining or modification of proteins. In particular, the present invention relates to covalent fluorescence complementation assays for the detection of modified (e.g., ubiquitinated) proteins. The present invention further relates to the use of such covalent fluorescence assays in drug screening and research applications. The below description uses ubiquitination of substrates as an exemplary embodiment of the present invention. The present invention is not limited to the detection of ubiquitination events, but rather is suitable for the detection of all covalent conjugation between proteins.

The small peptide ubiquitin is covalently linked to lysine residues on many proteins (Goldknopf et al., (1980) J. Biol. Chem. 255, 10555-10558; Pickart, (2004) Cell 116, 181-190). Ubiquitination was originally identified as a signal for proteasomal degradation (McGuire et al., supra (1988) Arch. Biochem. Biophys. 262, 273-285; Driscoll et al., (1990) J. Biol. Chem. 265, 4789-4792). It also regulates other cellular processes, including protein trafficking and transcription activation (Hicke and Riezman, (1996) Cell 84, 277-287; Salghetti et al., (2001) Science 293, 1651-1653; Babst et al., (2000) Traffic 1, 248-258; Conaway et al., (2002) Science 296, 1254-1258; von der Lehr et al., (2003) Mol. Cell 11, 1189-1200). Several peptides related to ubiquitin have been identified (Kumar et al., (1993) Biochem. Biophys. Res. Commun. 195, 393-399; (1997) Cell 88, 97-107; Schwartz et al., (2003) Trends Biochem. Sci. 28, 321-328). Modifications by different peptides have distinct effects on the functions of the modified proteins.

Many transcription regulatory proteins can be modified by ubiquitin family peptides (Salghetti et al., (2001) Science 293, 1651-1653; Conaway et al., (2002) Science 296, 1254-1258; von der Lehr et al., (2003) Mol. Cell 11, 1189-1200; Treier et al., (1994) Cell 78, 787-798; Musti et al., (1997) Science 275, 400-402; Wertz et al., (2004) Science 303, 1371-1374; Nateri et al., (2004) Science 303, 1374-1378; Seeler and Dejean, A. (2003) Nat. Rev. Mol. Cell. Biol. 4, 690-699; Kaiser et al., (2000) Cell 102, 303-314; Muller et al., (1998) EMBO J. 17, 61-70; Ross et al., (2002) Mol. Cell 10, 831-842; Fogal et al., (2000) EMBO J. 19, 6185-6195; Rodriguez et al., (1999) EMBO J. 18, 6455-6461). Ubiquitination is thought to control the rates of transcription factor turnover by targeting them for degradation by proteasomes (Treier et al., supra; Musti et al., supra; Wertz et al., supra; Nateri et al., supra). However, ubiquitination can also regulate transcription through mechanisms other than transcription factor degradation (Salghetti et al., supra; von der Lehr et al., supra; Kaiser et al., supra). Ubiquitin family peptides have been implicated in the control of the subnuclear localization of transcription factors (Muller et al., supra; Ross et al., supra; Fogal et al., supra; Rodrieguez et al., supra). The relationship between the control of subcellular localization and the regulation of transcription activation remains to be elucidated.

Jun is a transcription regulatory protein whose expression is induced by many extracellular stimuli (Vogt, (2002) Nat. Rev. Cancer 2, 465-469). The transient response of the cell to these stimuli is controlled in part by the rapid degradation of Jun after synthesis. Jun ubiquitination has been studied in both cell extracts and reconstituted ubiquitination reactions (Treier et al., (1994) Cell 78, 787-798; Musti et al., (1997) Science 275, 400-402; Wertz et al., (2004) Science 303, 1371-1374; Nateri et al., (2004) Science 303, 1374-1378). Ubiquitinated Jun is thought to be degraded by proteasomes because proteasome inhibitors stabilize Jun (Wertz et al., supra). Prior to the present invention, ubiquitinated Jun had not been directly visualized in living cells, and alternative pathways for Jun degradation had not been investigated.

Experiments conducted during the course of development of the present invention resulted in the direct visualization of ubiquitinated Jun in living cells using an ubiquitin-mediated covalent fluorescence conjugation assay (UbFC). The approach uncovered a new pathway for Jun degradation mediated by ubiquitination by Itch and translocation to endolysosomal vesicles. The exclusion of ubiquitinated Jun from the nucleus provides a mechanism for rapid abolition of its transcriptional activity. The present invention is not limited to a particular mechanism. Indeed, an understanding of the mechanism is not necessary to practice the present invention. Nonetheless, it is contemplated that sequestration of ubiquitinated Jun to endolysosomal vesicles can prevent reactivation of the protein by ubiquitin hydrolases and may be beneficial under conditions when protein degradation is inefficient due to limiting ATP or other factors.

In the analysis of the effects of ubiquitin family peptide conjugation on protein localization using the UbFC approach, it preferred that the fluorescent protein fragment fusions do not affect localization of the conjugate. In the case of Jun, the results of UbFC analysis and subcellular fractionation using proteins without fluorescent protein fragment fusions produced concordant results. The fusion proteins also exhibited subcellular distributions indistinguishable from those of proteins lacking the fusions, and the Jun fusion had a turnover rate comparable to that of endogenous Jun.

Further experiments conducted during the course of development of the present invention demonstrated that the Y170F mutation that prevented Jun ubiquitination by Itch reduced the rate of Jun degradation by >70%. The Itch recognition motif was therefore required for the major pathway of Jun degradation in COS-1 cells. The $^{167}PPVY^{170}$ recognition sequence for Itch overlaps a putative phosphorylation site for Abl kinase in Jun (Barila et al., (2000) EMBO J. 19, 273-281). Phosphorylation of this tyrosine by Abl or other tyrosine kinases could regulate recognition of Jun by Itch/AIP4 or other HECT family E3 ligases. Two other E3 ligases that can ubiquitinate Jun have been identified (Wertz et al., supra; Nateri et al. supra). The SCFFbw7 E3 ligase specifically recognizes Jun phosphorylated by JNK (Nateri et al., supra). Overexpression of the $DC^{hDET1-hCOP1}$ E3 ligase reduced the level of Jun, and depletion of individual components of the complex increased the half-life of Jun by ≈30% (Wertz et al., supra). The multisubunit SCFFbw7 and $DCX^{hDET1-hCOP1}$ RING-type E3 ligases are structurally unrelated to the single-polypeptide HECT-type E3 ligase Itch. They recognize Jun sequences that are >50 amino acid residues away from the $^{167}PPVY^{170}$ motif. The present invention is not limited to a particular mechanism. Indeed, an understanding of the mechanism is not necessary to practice the present invention. Nonetheless, it is contemplated that it is unlikely that the Y170F mutation in Jun affected ubiquitination by these RING-type E3 ligases. Jun ubiquitinated by $DCX^{hDET1-hCOP1}$ is thought to be degraded by proteasomes, because degradation in cells that overexpressed this E3 ligase is inhibited by MG132 (Wertz et al., supra). The use of several ubiquitin ligases and degradation pathways for the regulation of Jun stability provides the potential for control of Jun turnover through multiple independent mechanisms.

Accordingly, in some embodiments, the present invention provides ubiquitin-mediated covalent fluorescence conjugation assays for the detection of ubiquitinated proteins. The methods and compositions of the present invention find use, for example, in drug screening (e.g., to screen for drugs that alter ubiquitination of proteins) and research (e.g., to identify ubiquitinated proteins and ubiquitination pathways). The methods of the present invention provide the particular advantage of functioning in living cells. Thus, the methods of the present invention allow direct visualization of covalent conjugations in their native physiological environment. The assay is also functional in multiple sub-cellular locations of eukaryotic (e.g., mammalian) cells, allowing for the detection of a specific location of a given ubiquitinated or otherwise covalently modified protein. The assays of the present invention utilize an intrinsic property of a protein (e.g., fluorescence) and thus do not require additional co-factors or experimental steps to visualize results. Furthermore, the methods of the present invention are applicable to multiplexing via different color fluorescence emissions. The present invention thus provides novel methods (e.g., drug screening methods) for the investigation of ubiquitination and screening for inhibitors or potentiators of such interactions.

The below description provides exemplary non-limited methods, compositions and uses of the present invention. One skilled in the relevant arts understands that the present invention is not limited to the embodiments described herein.

I. Fluorescence Assays

In some embodiments, the present invention provides methods and compositions for performing ubiquitin mediated covalent fluorescence conjugation (UbFC) assays. The assays of the present invention are able to be performed in living cells, and require minimal perturbation of cells.

The below description provides a non-limiting description of illustrative embodiments of the present invention. One skilled in the relevant arts recognizes that the present invention encompasses variations of the below described compositions and methods.

A. Fluorescence Complementation Assay

In some embodiments, the present invention provides compositions and methods for performing ubiquitin mediated covalent fluorescence complementation assay. Preferably UbFC assays utilize two fusion proteins (See e.g., experimental section). Preferably, each of the fusion proteins comprises a fragment of a fluorescent protein and a conjugation partner (e.g., ubiquitin or a candidate protein for ubiquitination), optionally joined by a linker sequence. Covalent conjugation of the target proteins allows for the association of the fragments of the fluorescent proteins, resulting in visible fluorescence signal.

The fluorescence assays of the present invention are not limited to particular fluorescent proteins or particular protein fragments. The present invention is also not limited to particular binding partners or constructs for expressing binding partner-fluorescent protein fragments. Examples of suitable compositions for use in some embodiments of the present invention are described below.

A. Proteins

In some embodiments, the present invention utilizes naturally fluorescent proteins and fluorescent variants of such proteins for fragmentation and use in fluorescence conjugation assays. In some embodiments, variants of Green Fluorescent protein (EGFP) are utilized.

EGFP is a relatively small protein comprising 238 amino acids, and is the ultimate source of fluorescent light emission in the jellyfish Aequorea victoria (Prasher et al., (1992, Gene, 111:229-233). EGFP fluorescence in procaryotic and eucaryotic cells does not require exogenous substrates and cofactors. The EGFP excitation spectrum shows an absorption band (blue light) maximally at 395 mn with a minor peak at 470 nm, and an emission peak (green light) at 509 nm. The longer-wavelength excitation peak has greater photostability then the shorter peak, but is relatively low in amplitude (Chalfie et al., 1994, Science, 263:802-805). The crystal structure of the protein and of several point mutants has been solved (Ormo et al., 1996, Science 273, 1392; Yang et al., Nature Biotechnol. 14, 1246). The fluorophore, consisting of a tripeptide at residues 65-67, is buried inside a beta-barrel structure. The EGFP absorption bands and emission peak arise from an internal p-hydroxybenzylidene-imidazolidinone chromophore, which is generated by cyclization and oxidation of the tripeptide sequence Ser-Tyr-Gly sequence at residues 65-67 (Cody et al., 1993, Biochemistry 32:1212-1218).

In some embodiments, variants (e.g., mutants) of EGFP having altered fluorescent properties (e.g., fluorescence emission of a different visible wavelength) are utilized. Such proteins include, but are not limited to, those disclosed in U.S. Pat. Nos. 6,140,132, 6,316,223, 6,150,176, each of which is herein incorporated by reference, Haas et al., Curr. Biol. 6:315-324 (1996), Crameri et al., Nature Biotechnol. 14:315-319 (1996), each of which is herein incorporated by reference, and those commercially available.

B. Fragments

In some embodiments, the UbFC assays of the present invention utilize fragments of fluorescent proteins. The present invention in not limited to particular fragments or locations of fragmentation. Fluorescent proteins may be fragmented in any location that allows for the production of florescence in the UbFC assay. Candidate fragments may be tested, for example, using the methods disclosed herein (See e.g., experimental section). Preferred fragments are those that assemble in presence, but not the in the absence, of ubiquitination or other covalent modification of a protein.

In some preferred embodiments, C-terminal fragments of EEYFP that contain a T203Y substitution are utilized (e.g., SEQ ID NOs: 3 and 5). In some embodiments, such C-terminal fragments are paired with N-terminal fragments of EEYFP (e.g., SEQ ID NOs: 2 and 4), resulting in yellow fluorescence from the reassembled protein. The present invention is not limited to the use of C-terminal fragments of EEYFP. C-terminal fragments from any fluorescent protein are contemplated.

In other embodiments, C-terminal fragment of EEYFP (or other fluorescent proteins) are paired with N-terminal fragments from variants of EGFP having different colored emission spectrums (See e.g., Hu and Kerppola, Nature Biotechnology 21:539 [2003]; herein incorporated by reference). Such hybrid pairings result in a variety of colored fluorescence emission spectra that are suitable for use in multiplexing assays. For example, in some embodiments, an N-terminal fragment of ECFP (SEQ ID NO:6) or EYFP (SEQ ID NO:4) is paired with a C-terminal fragment of EYFP (SEQ ID NO:5). In other embodiments, the N-terminal fragment of EYFP (SEQ ID NO:4) or EGFP (SEQ ID NO: 7) is paired with a C-terminal fragment of EYFP (SEQ ID NO:5). In still further embodiments, the N-terminal fragment of Citrine (SEQ ID NO:8) is paired with a C-terminal fragment of EYFP (SEQ ID NO:5).

In still further embodiments, engineered GFP (e.g., Venus protein) fragments are utilized. Exemplary N and C-terminal fragments are described in FIG. 14 and SEQ ID NOs: 9,10, and 11.

C. Targets

The present invention is not limited to a particular protein (e.g., ubiquitin) target. Any protein or other biological molecule that is covalently modified by or is suspected of being covalently modified by ubiquitin or other proteins may be utilized. In some embodiments, libraries of target compounds are screened (e.g., in high throughput assays).

D. Constructs

In some embodiments, the present invention provides constructs for the expression of fusion proteins comprising nucleic acid sequences encoding the first and second fluorescent protein fragments fused to ubiquitin and ubiquitin target proteins. In some embodiments, the nucleic acid sequences encoding fusion proteins further comprise a linker sequence in between the nucleic acid sequence encoding the fragment of a fluorescent protein and the nucleic acid sequence encoding the binding partner. The present invention is not limited to particular linker sequence. In some embodiments, each of the fusion proteins is contained in a separate vector. In other embodiments, both of the fusion proteins are contained in the same vector. The choice of vector is dependent on the particular host cell chosen (e.g., prokaryotic or eukaryotic). In some preferred embodiments, vectors suitable for expression in mammalian cells are utilized.

In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually from about 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome-binding site for translation initiation and a transcription terminator. In still other embodiments of the present invention, the vector may also include appropriate sequences for amplifying expression.

E. Host Cells

In a further embodiment, the present invention provides host cells containing the above-described constructs. In some preferred embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell is a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C 127, 3T3, 293, 293T, HeLa and BHK cell lines.

The constructs in host cells can be used in a conventional manner to produce the fusion proteins encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the fusion polypeptides of the invention can be synthetically produced by conventional peptide synthesizers.

Fusion proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifigation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

F. Expression in Organisms

In some embodiments, the present invention provides methods of conducting ubiquitin mediated covalent fluorescence conjugation experiments in tissues or live animals or plants. For example, in some embodiments, the methods of the present invention find use in determining the particular organ in which ubiquitination occurs or ubiquitinated proteins are found (e.g., by observing the location of a fluorescent signal). In some embodiments, the fluorescent signal is observed by observing the animal or plant directly (e.g., when fluorescence is expressed in the skin). In other embodiments, in vivo imaging techniques are utilized to observe fluorescence. In some embodiments, vectors expressing the fusion protein of interest are targeted to specific tissue types or organs.

Viral vectors commonly used for in vivo or ex vivo expression procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (e.g., on the isolated DNA) or in situ, using the techniques of genetic manipulation or by treatment with mutagenic agents. Retroviral vectors as well as retrotransposons may also be used to produce genomic fusions in which the sequences encoding the fragments of the fluorescent proteins are fused directly to genomic sequences encoding normal cellular proteins.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski etal., J. Virol., 61:3096-3101 [1987]; Samulski etal., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mavl, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the El region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et aL., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors comprising the fusion protein of the present invention can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

G. Kits

In some embodiments, the present invention provides kits for performing ubiquitin mediated covalent fluorescence conjugation assays. In some embodiments, the kits contain at least one vector encoding a ubiquitin fused to a first fluorescent protein fragment. In some embodiments, the kits comprise a second vector encoding a second fusion protein that encodes a second protein fragment (e.g., ubiquitin target) and the second binding partner. In other embodiments, the kits comprise a single vector encoding the first and second fusion proteins. In preferred embodiments, the kits contain all of the components necessary to perform a UbFC assay, including all controls, directions for performing assays, and any necessary software for analysis and presentation of results.

II. Applications of Ubiquitin-Mediated Fluorescence Complementation

The UbFC assays of the present invention find use in a variety of applications where one is interested in identifying a covalent conjugation. In other embodiments, UbFC assays are utilized to identify compounds that inhibit known covalent conjugations (e.g., for drug screening or to identify cellular signaling pathway inhibitors for research applications). In other embodiments, UbFC assays are used to identify a tissue or intracellular location of a covalent conjugation.

A. Detection of Fluorescence.

Fluorescence signal can be detected using any suitable method. For example, in some embodiments (e.g., to detect a particular sub-cellular location of a covalent conjugation), confocal microscopy is utilized. In other embodiments, a fluorescence spectrophotometer is utilized. In embodiments utilizing multiplexed reactions exhibiting multiple colors of fluorescence, detection may be accomplished using a confocal microscope to observe the different colors. Alternatively, a microscope or a fluorescence spectrophotometer comprising multiple color filters or detectors may be utilized. In some embodiments, qualitative measurements of fluorescence intensity are obtained. In other embodiments, quantitative measurements are obtained.

In some embodiments, kinetic fluorescence measurements are obtained. Such measurements are typically obtained using a fluorimeter. Multiplexed kinetic measurements may be obtained using a fluorimeter comprising multiple color filters or detectors.

In still further embodiments, fluorescent activated cell sorting (FACS) is used to separate cells exhibiting a fluorescent signal from those that do not. The use of FACS allows for the screening of large populations of cells for cells that exhibit fluorescence.

In yet other embodiments, high throughput and/or automated systems are utilized for the simultaneous analysis of multiple UbFC assays. For example, in some embodiments, such systems are configured for detection using multi-well plates, array, automated solution handling (e.g., robotics), etc.

B. Screens for Ubiquitination Targets

In some embodiments, the present invention is used to screen potential proteins for ubiquitination. As described above, in some embodiments, the present invention provides UbFC assays for detecting ubiquitination of target proteins. In some embodiments, assays are performed in vitro. In other embodiments, assays are performed in cell culture (e.g., mammalian cell culture). In some embodiments, flow cytometry (e.g., FACS) is used to screen large libraries of potential ubiquitination targets (e.g., from genetic libraries).

C. Drug Screening

In some embodiments, the present invention provides drug-screening assays (e.g., to screen for drugs that inhibit or enhance ubiquitination of a target). For example, in some embodiments, a UbFC assay is designed between a known ubiquitin target and ubiquitin. Libraries of compounds are screened for their ability to inhibit the covalent conjugation of the proteins and/or to identify a cellular location of a covalent conjugation.

In some embodiments, drug-screening assays are conducted in vitro. In some embodiments, fusion proteins are expresses and purified prior to the fluorescence conjugation assay. In other embodiments, in vitro transcription and translation systems are utilized. In other embodiments, drug-screening assay are performed in cell culture (e.g., in mammalian cell culture). In still further embodiments, assays are performed in live animals.

In some preferred embodiments, high throughput drug screening assays are performed. Both in vitro, in vivo, and cell culture assays are amenable to high throughput screening methods. In certain embodiments, multiplexed drug screening assays are utilized to screen multiple covalent conjugations simultaneously.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Natl. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl.' 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

D. Localization of Ubiquitination

In still further embodiments, the UbFC assays of the present invention are utilized for the detection of the sub-cellular localization of ubiquitinated proteins. In some embodiments, mammalian cells are utilized for such assays. The constructs of interest are introduced into cells and the sub-cellular location of the fluorescence is detected (e.g., using confocal microscopy). In some embodiments, such methods are used to screen for the effect of variant target proteins on the location of a covalent conjugation. In other embodiments, test compounds (e.g., drugs) are administered to the cells along with the vectors containing nucleic acid sequences encoding UbFC partners and the effect of the test compound on the location of the covalent conjugation is determined. In still further embodiments, libraries of compounds are administered to cells comprising fusion partners known to produce covalent protein conjugates or engineered to conjugate in a particular sub-cellular location and the effect of the test compounds on fluorescence is detected. Such assays find use in screening compounds (e.g., drugs) for their ability to access a particular sub-cellular location or organelle.

G. Live Animals

In yet other embodiments, the UbFC methods of the present invention are utilized to detect ubiquitination in live animals. Vectors comprising nucleic acids encoding fusion proteins may be generated and introduced into animals as described above. In some embodiments, fluorescence conjugation assays are used to characterize the location (e.g., tissue, organ or region of an organ) of a particular ubiquitination event. In other embodiments, UbFC is used for drug screening assays in animals as described above.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); and ° C. (degrees Centigrade).

EXAMPLE 1

This Example describes the development and application of ubiquitin mediated fluorescence complementation assays.

Plasmid Construction. The sequences encoding amino acids residues 1-172 of enhanced yellow fluorescent protein and enhanced cyan fluorescent protein (ECFP) (Clontech) were fused to the 5' ends of the coding regions for ubiquitin and small ubiquitin-related modifier 1 (SUMO1) by using ANSSIDLISVPVEYPYDVPDYASR (SEQ ID NO:1) linkers. The chimeric coding regions were cloned into the pFLAG-CMV2 (Sigma) to produce plasmids encoding YN-Ub, YN-SUMO1, and CN-SUMO1. The plasmids encoding Jun and Jun257-318 fused to amino acid residues 155-238 of ECFP were as described (Hu et al., (2002) Mol. Cell 9, 789-798; Hu et al., (2003) Nat. Biotechnol. 21, 539-545) and are designated Jun-CC and bJun-CC. The plasmid encoding Jun-CFP was constructed by inserting the coding region of Jun into pECFP (Clontech). The Y170F mutation in Jun (JunY170F), the deletion of G100 and G101 in SUMO1 (SUMOΔG), and the K48R, K63R, G75K, and G76L mutations in ubiquitin (Ub-Mut) were generated by using PCR and were confirmed by DNA sequencing.

Cells and Antibodies. COS-1, NIH 3T3, and HEK293T cells were cultured as recommended by the American Type Culture Collection. Polyclonal anti-c-Jun, anti-Rab6, anti-TSG101, anti-Myc, and antihemagglutinin antibodies were from Santa Cruz Biotechnology. Monoclonal LAMP1 (Clone H4A3), LAMP2 (clone ABL-93) (Hybridoma Bank at the University of Iowa), anti-Xpress (Invitrogen), and anti-Flag (Sigma) antibodies were used.

Analysis of Fluorescence Complementation. Cells transfected with plasmids encoding the indicated combinations of fusion proteins were incubated at 37° C. for 24 h and then transferred to 30° C. for 4-16 h to promote fluorophore maturation. The fluorescence emissions of the cells were imaged as described (Hu et al., (2002) Mol. Cell 9, 789-798; Hu et al., (2003) Nat. Biotechnol. 21, 539-545).

Immunofluorescence and Confocal Analysis. Cells transfected with plasmids encoding the indicated combination of fusion proteins were fixed with 3.7% paraformaldehyde after 36 h. Fixed cells were washed with 0.1% Triton X-100 and incubated with the antibodies indicated followed by secondary antibody labeled with Alexa Fluor 594. Fluorescence images were collected by confocal microscopy.

Immunoprecipitation, Immunoblotting, and Metabolic Labeling. Extracts were prepared from COS-1 cells transfected with the plasmids indicated. The extracts were analyzed by immunoprecipitation and immunoblotting as described (Fang et al., (2002) Nat. Immunol. 3, 281-287). Metabolic labeling with [35S]methionine/[35S]cysteine and pulse-chase analysis were performed as described (Fang et al., supra).

Cell Fractionation and Lysosome Isolation. Cells were lysed in hypotonic buffer as described (Fang et al., supra). The nuclei were pelleted by centrifugation at 3,000×g for 5 min. The nuclear pellet was resuspended in 1% Nonidet P-40 cell lysis buffer, and insoluble material was removed by centrifugation at 16,000×g for 10 min. Lysosomes were purified by Percoll density gradient sedimentation, and β-hexosaminidase activity was measured as described (Green et al., (1987) J. Cell Biol. 105, 1227-1240).

B. Results

Visualization of Ubiquitination in Living Cells. Ubiquitination is generally detected by immunoprecipitation followed by Western blot analysis using antibodies directed against epitope tags linked to ubiquitin and to a putative substrate protein (Finley et al., (1984) Cell 37, 43-55). This approach has the inherent limitation that it does not allow analysis of ubiquitination in living cells. The study of ubiquitination in cells is further impeded by the small subpopulation of each protein that is ubiquitinated at any one time.

To develop an approach for the visualization of specific ubiquitinated proteins in living cells, the ability of fragments of selected fluorescent proteins to form a fluorescent complex when brought together by the association of proteins fused to the fragments (Hu et al., (2002) Mol. Cell 9, 789-798; Hu et al., (2003) Nat. Biotechnol. 21, 539-545) was utilized. The present Example utilized the fusion of ubiquitin to one fragment of a fluorescent protein, as well as a putative substrate to the complementary fragment, to allow selective visualization of the ubiquitin conjugate in living cells. This approach is designated ubiquitin-mediated fluorescence complementation (UbFC).

To test the feasibility of the UbFC approach, the N-terminal fragment of the yellow fluorescent protein was fused to ubiquitin and the complementary fragment to Jun. Plasmids encoding both fusion proteins were transfected into COS-1 cells, and the cells were observed by fluorescence microscopy. Cells transfected with both plasmids, but not cells transfected with either plasmid alone, were fluorescent (FIG. 1A Left). The fluorescence was located mainly outside the nucleus and was concentrated in small spherical structures in the cytoplasm, including an aggregation of these structures that was frequently adjacent to the nucleus. Similar patterns of fluorescence complementation were observed when the fusion proteins were expressed in HEK293T or NIH 3T3 cells. To ascertain that expression of the fusion proteins did not disrupt the normal mechanisms for Jun localization, Jun fused to full length CFP was expressed in the same cells. Jun-CFP was localized mainly to the nucleus (FIG. 1A Center). The present invention is not limited to a particular mechanism. Indeed, an understanding of the mechanism is not necessary to practice the present invention. Nonetheless, it is contemplated that these results suggest that ubiquitination of Jun caused export from the nucleus into discrete cytoplasmic structures.

Different ubiquitin family peptides have distinct biological effects when conjugated to substrate proteins. The effect of the SUMO1 on Jun in cells was examined using the UbFC assay. Expression of SUMO1 and Jun fused to complementary fluorescent protein fragments produced fluorescence that was localized to subnuclear foci (FIG. 1B Left). Coexpressed Jun-CFP was distributed throughout the nucleoplasm and enriched in nucleoli (FIG. 1B Center). The results of these experiments indicate that SUMO1 conjugation induced Jun localization to specific subnuclear structures.

The distinct subcellular locations of the fluorescent complexes formed by Jun with ubiquitin versus SUMO1 suggest that different modifications have distinct effects on Jun localization. To compare the effects of these modifications in the same cell, a multicolor adaptation of the UbFC assay (Hu et al., (2003) Nat. Biotechnol. 21, 539-545) was utilized. Ubiquitin and SUMO1 fused to fragments of different fluorescent proteins were co-expressed with Jun fused to a complementary fragment. The ubiquitin and SUMO1 conjugates of Jun exhibited nonoverlapping distributions similar to those that were observed when the conjugates were produced in separate cells (FIG. 1C). The distinct subcellular distributions of these conjugates were therefore not caused by distinct cellular responses to the expression of ubiquitin versus SUMO1 but were determined by intrinsic localization determinants on these conjugates.

The UbFC approach requires fusion of fluorescent protein fragments to the ubiquitin family peptide as well as to the putative substrate. It was examined whether fusion of the fluorescent protein fragments to ubiquitin and SUMO1 affected their conjugation to substrate proteins. Western blot analysis of extracts from cells that expressed ubiquitin fused to a fluorescent protein fragment produced a high-molecular-weight smear of conjugates that was of similar intensity but of higher apparent molecular weight compared with that observed when extracts from cells that expressed epitope-tagged ubiquitin were analyzed. Western blot analysis of anti-Jun immunoprecipitates from cells expressing SUMO1 fused to a fluorescent protein fragment produced two bands of similar intensities to those observed when SUMO1 lacking the fusion was expressed (FIG. 7B). It is contemplated that the two bands correspond to Jun modified at one or two lysine residues. The fraction of Jun modified at two sites was much higher than predicted if the sites were modified independently. Thus, ubiquitin and SUMO1 fused to the fluorescent protein fragment were conjugated to substrates as efficiently as the peptides lacking the fusions.

Figure 2:
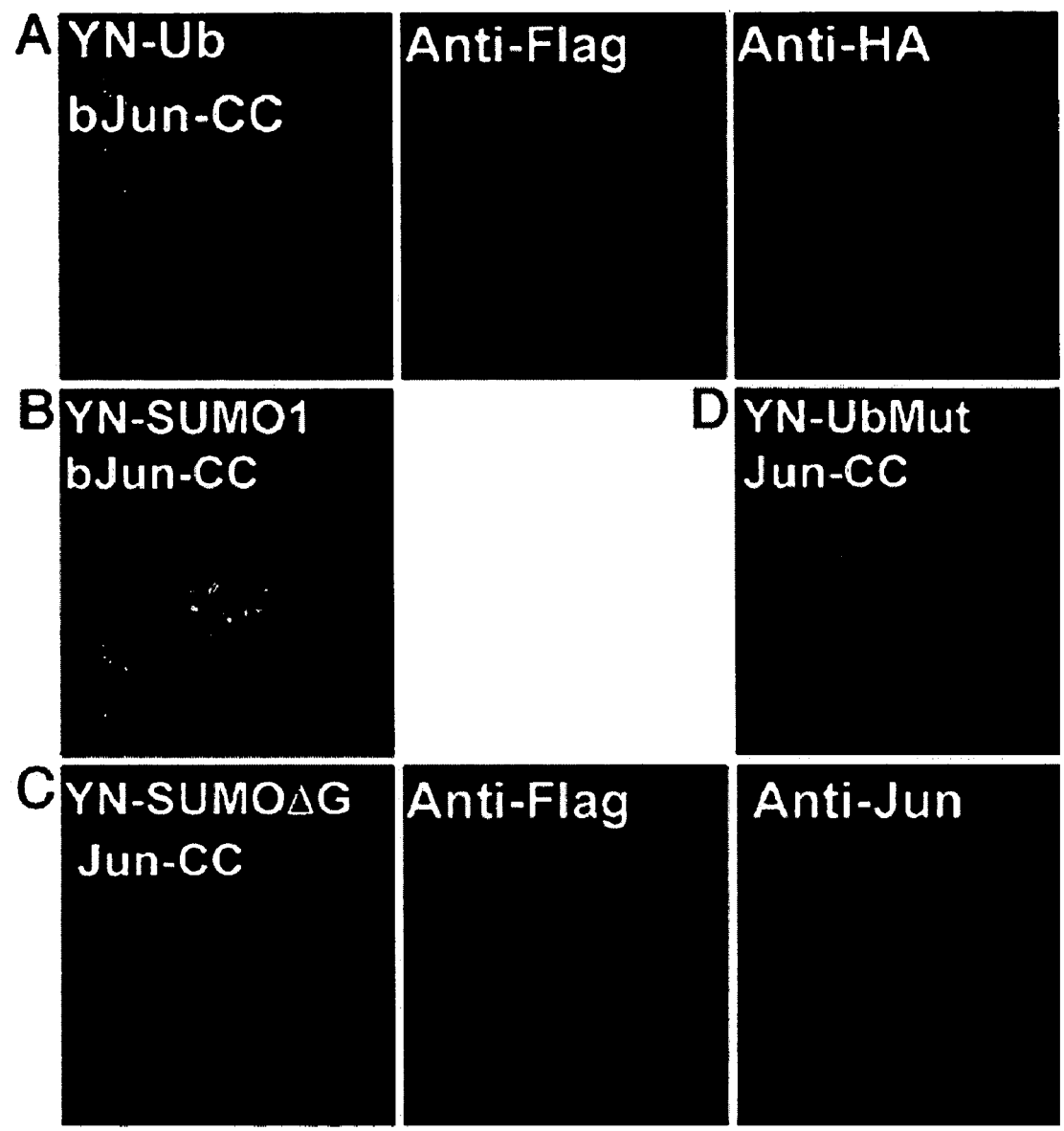
FIG. 2 shows specificity of the UbFC assay. (A) YN-Ub and bJun-CC; (B) YN-SUMO1 and bJun-CC; (C) YN-SUMO1ΔG and Jun-CC; and (D) YN-UbMut and Jun-CC were expressed in COS-1 cells.

The distinct distributions of the fluorescent complexes formed by Jun with ubiquitin versus SUMO1 suggested that the complexes represented specific conjugates. To ascertain the specificity of the UbFC assay, the effects of mutations on fluorescence complementation were examined. Deletion of regions of Jun outside the bZIP domain eliminated fluorescence complementation with ubiquitin but did not prevent fluorescence complementation with SUMO1 (FIGS. 2A and B). The level of ubiquitination of the bZIP domain of Jun detected by Western blot analysis of cell extracts was >10-fold lower than that of full length Jun. The selective loss of fluorescence complementation caused by deletion of regions outside the bZIP domain of Jun corroborates the specificity of the UbFC assay of Jun ubiquitination.

Fluorescence complementation can be facilitated by the covalent or noncovalent association of proteins fused to the fluorescent protein fragments. The effects of mutations that prevented conjugation on fluorescence complementation were examined. Deletion of the C-terminal glycines of SUMO1 eliminated the fluorescence complementation with Jun (FIG. 2C). This mutation also eliminated the SUMO1 conjugates of Jun detected in cell extracts (FIG. 7B). The fusions were expressed in overlapping regions of the cell, and the level of expression of mutated SUMO1 was comparable to that observed for the wild-type peptide. The lack of fluorescence complementation therefore indicates that the complementation observed in the UbFC assay reflected the covalent conjugation of SUMO1 to Jun. When mutated ubiquitin fused to the N-terminal fragment of yellow fluorescent protein was expressed with Jun fused to the complementary fragment, fluorescence complementation was detected (FIG. 2D). This fluorescence was localized predominantly to the nucleus and exhibited a distribution identical to that of unmodified Jun. No covalent conjugates of the mutated ubiquitin were detected in cell extracts, indicating that the complementation resulted from noncovalent association of the fusion proteins. The nonconvalent bimolecular fluorescent complexes formed by mutated ubiquitin with Jun were exclusively nuclear, indicating that the cytoplasmic localization of complexes formed by wild-type ubiquitin required covalent conjugation to Jun.

Fluorescence complementation requires that the fragments of the fluorescent protein can associate with each other in the complex. To examine whether conjugates with different steric arrangements of the fluorescent protein fragments had different subcellular distributions, complementation using proteins in which the fluorescent protein fragments were fused to different ends of Jun was examined. These proteins formed fluorescent complexes with ubiquitin that exhibited identical subcellular distributions. No fluorescence complementation was observed when Jun fused to a fluorescent protein fragment on the N-terminal end was expressed together with SUMO1 fused to the complementary fragment (FIG. 8D).

The difference between the effects of the position of the fusion on fluorescence complementation with ubiquitin versus SUMO1 is consistent with the greater reach and flexibility predicted for a polyubiquitin chain relative to a mono-SUMO1 adduct.

Figure 3:
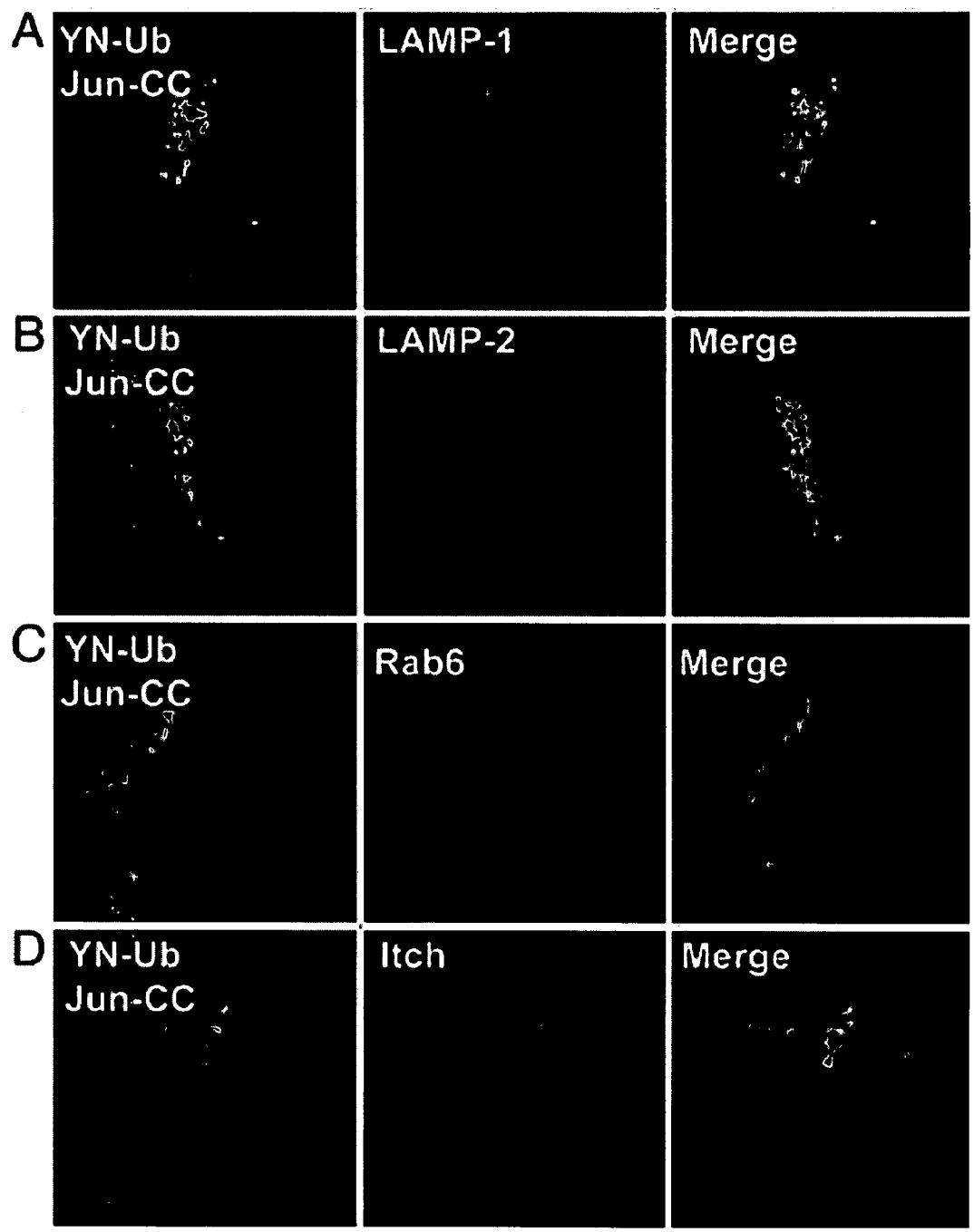
FIG. 3 shows the subcellular localization of ubiquitinated Jun. YN-Ub and Jun-CC were expressed in COS-1 cells, and cells fixed 36 h after transfection were immunostained with antibodies directed against (A) LAMP1, (B) LAMP2, (C) Rab6, or (D).

Subcellular Localization of Ubiquitinated Jun. To identify the subcellular compartment where ubiquitinated Jun was localized, the locations of fluorescence complementation was compared with those of cellular proteins with known subcellular distributions. Because ubiquitin-conjugated Jun was distributed in a pattern reminiscent of transport vesicles, its localization was compared with markers for various endosomal compartments. Ubiquitinated Jun closely colocalized with the LAMP1 and LAMP2 lysosomal membrane proteins (FIGS. 3A and B) (Chen et al., (1985) J. Cell Biol. 101, 85-95). There was no colocalization of ubiquitin-conjugated Jun with the small GTPase Rab6, which participates in vesicular sorting in the Golgi and endoplasmic reticulum (Tisdale et al., (1992) J. Cell Biol. 119, 749-761) (FIG. 3C). These results suggest that ubiquitin-conjugated Jun is localized to lysosomes.

Figure 4:
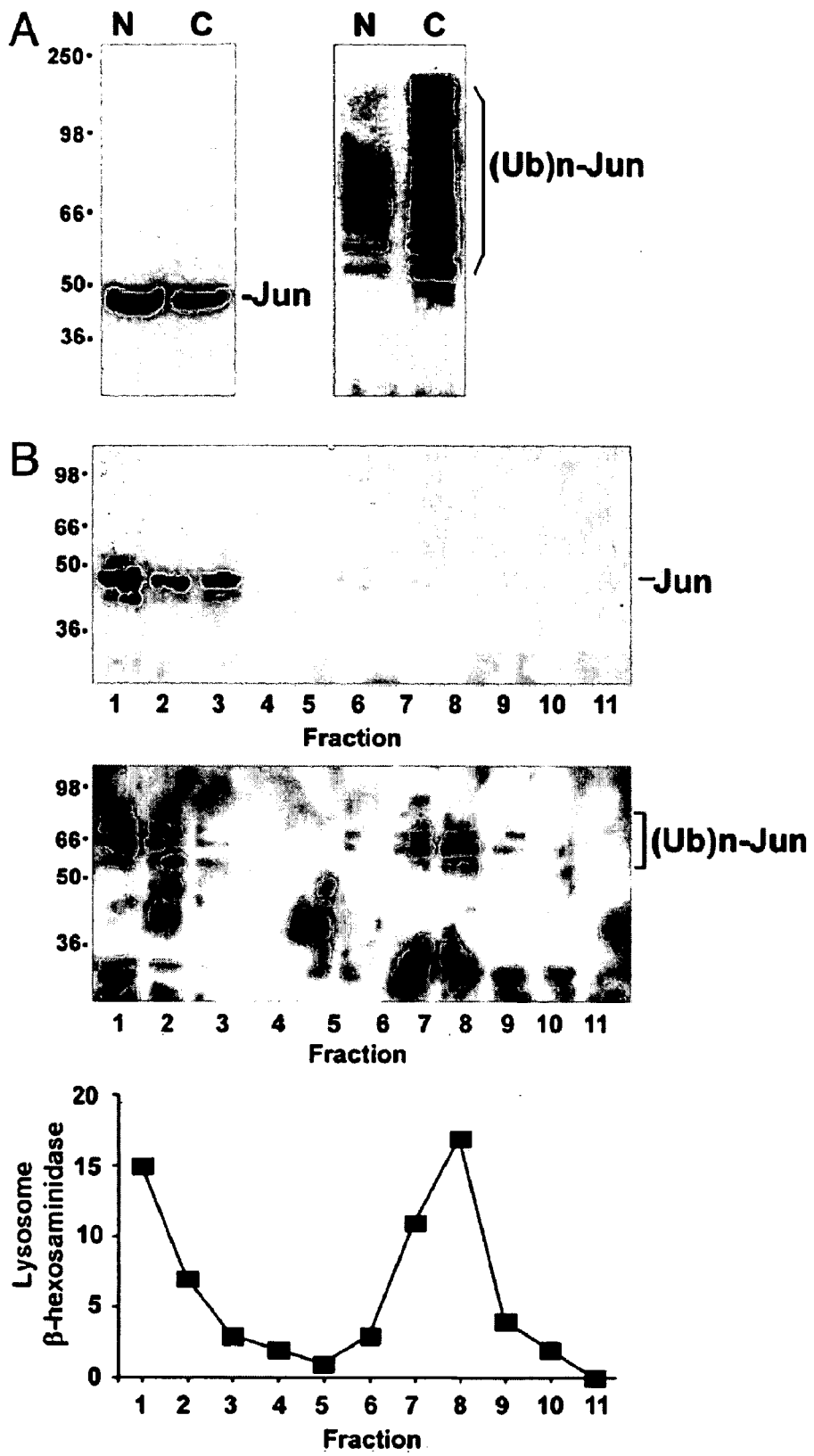
FIG. 4 shows subcellular fractionation of ubiquitinated Jun. (A) Nuclear and cytoplasmic fractions were prepared from cells that expressed Jun and ubiquitin tagged with the Xpress and hemagglutinin (HA) epitope tags, respectively. (B) The cytoplasmic extract was fractionated by density gradient sedimentation. Total Jun (Upper) and ubiquitinated Jun (Lower).

To complement the visualization of ubiquitinated Jun in living cells, the fractionation of ubiquitinated Jun in cell lysates was examined. Extracts from cells that expressed epitope-tagged Jun and ubiquitin were separated into nuclear and cytoplasmic fractions. The majority of unmodified Jun was found in the nuclear fraction (FIG. 4A Left). Most of the ubiquitinated Jun was found in the cytoplasmic fraction (FIG. 4A Right). Because these experiments were performed by using Jun and ubiquitin that were not fused to fluorescent protein fragments, the results demonstrate that the cytoplasmic localization of the conjugate was independent of fluorescent complex formation. The majority of ubiquitinated endogenous Jun was also found in the cytoplasmic fraction. The partitioning of ubiquitinated Jun into the cytoplasmic fraction is consistent with the cytoplasmic localization of the UbFC conjugate in living cells.

To examine whether the ubiquitinated Jun in cell lysates was associated with lysosomes, the cytoplasmic fraction was analyzed by density gradient sedimentation. Lysosomes have a high density and sediment toward the bottom of the gradient, whereas other membranes and soluble proteins have a lower density and sediment near the top of the gradient. Virtually all unmodified Jun was recovered in the top three fractions (FIG. 4B Top). Ubiquitinated Jun separated into two populations, one at the top and a second toward the bottom of the gradient (FIG. 4B Middle). The location of lysosomes in the gradient was determined by measuring lysosomal β-hexosaminidase activity (FIG. 4B Bottom). β-hexosaminidase activity cosedimented in all fractions with ubiquitinated Jun. The ubiquitinated Jun and β-hexosaminidase activity at the top of the gradient may be due to lysis of part of the lysosomes during cell extraction. The cofractionation of ubiquitinated Jun with lysosomal β-hexosaminidase is consistent with the lysosomal localization of the conjugate detected by UbFC analysis.

Identification of the E3 Ligase That Ubiquitinated Jun in Cells. Several different E3 ligases can facilitate Jun ubiquitination in reconstituted reactions in vitro and subunits of these E3 ligases can interact with Jun in cell extracts (Wertz et al., (2004) Science 303, 1371-1374; Nateri et al., (2004) Science 303, 1374-1378). Experiments were designed to identify the E3 ligase(s) that mediated the ubiquitination of Jun detected in living cells. Both Jun and JunB can interact with the E3 ligase Itch in cell extracts, and Itch overexpression increases the level of JunB ubiquitination detected by Western analysis (Fang et al., (2002) Nat. Immunol. 3, 281-287). Itch is localized to lysosomes in some cells (Angers et al., (2004) J. Biol. Chem. 279, 11471-11479). The distributions of ubiquitin-conjugated Jun and Itch in COS-1 cells were compared (FIG. 3D). The majority of ubiquitinated Jun was localized to compartments that also contained high levels of Itch.

Figure 5:
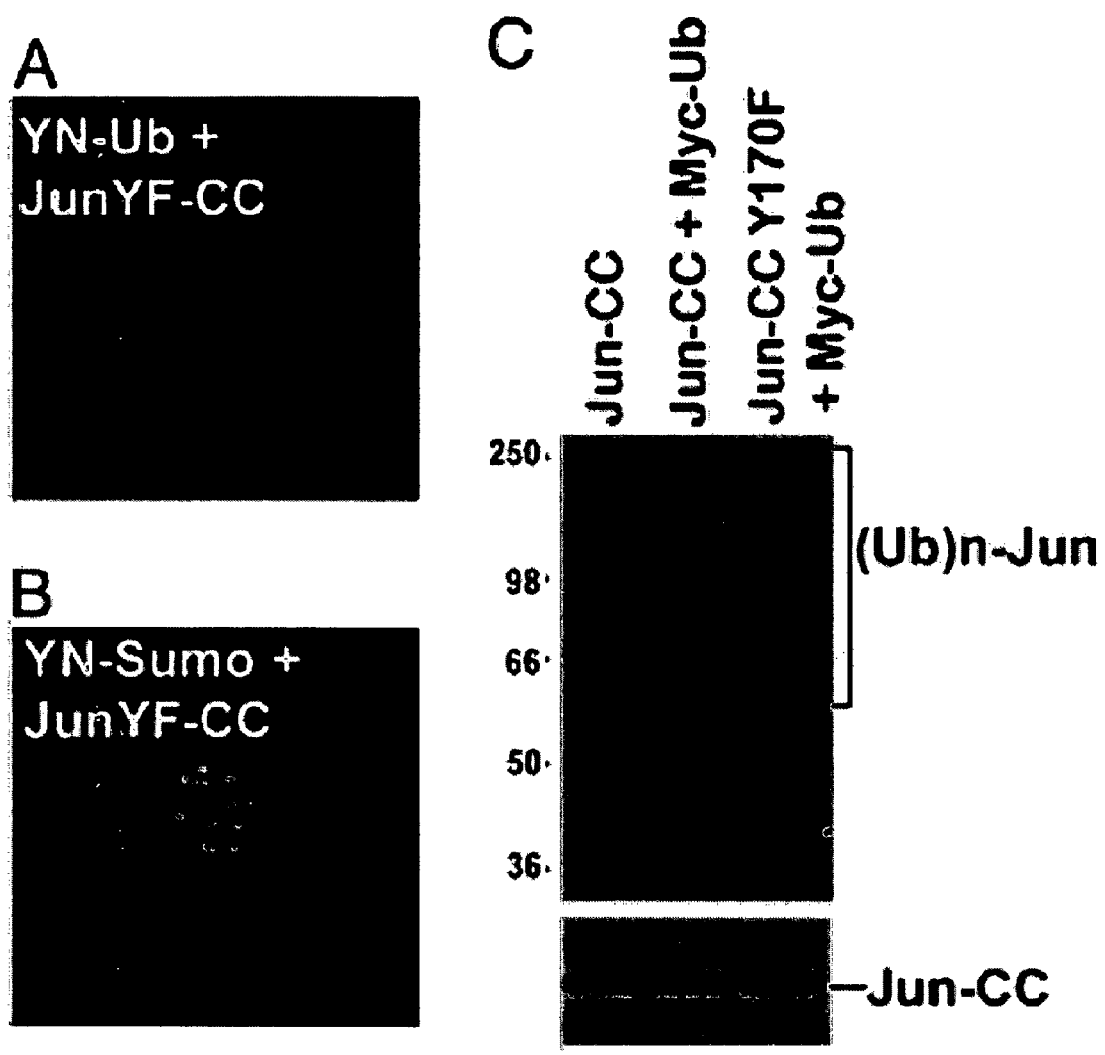
FIG. 5 shows specificity of Jun ubiquitination by Itch in living cells and cell extracts. (A) YN-Ub and JunY170F-CC or (B) YN-SUMO1 and JunY170F-CC were expressed in COS-1 cells, and fluorescence images were acquired 36 h after transfection. (C) The proteins indicated above each lane were expressed in HEK293T cells.

To determine whether Itch was responsible for the ubiquitination of Jun in cells, mutations in Jun that prevented its recognition by Itch were generated. Jun contains a sequence resembling the Itch recognition motif (167PPVY170) within the N-terminal region required for ubiquitination. A single amino acid substitution in this sequence (Y170F) eliminated fluorescence complementation with ubiquitin (FIG. 5A). The fusion proteins were coexpressed in the same cells and exhibited overlapping distributions. Coexpression of JunY170F with SUMO1 fused to the same fragments produced fluorescence complementation identical to that observed for wild-type Jun (FIG. 5B). Similar results were obtained in both COS-1 and HEK293T cells. Elimination of the Itch recognition sequence in Jun selectively abolished fluorescence complementation with ubiquitin in living cells. The role of Itch in Jun ubiquitination was also examined by Western blot analysis. The Y170F mutation dramatically reduced the level of ubiquitinated Jun detected in cell extracts (FIG. 5C). Taken together, the results of these experiments suggest that Jun ubiquitination in these cells is catalyzed primarily by Itch and/or E3 ligases that recognize the same sequence motif in Jun.

Figure 6:
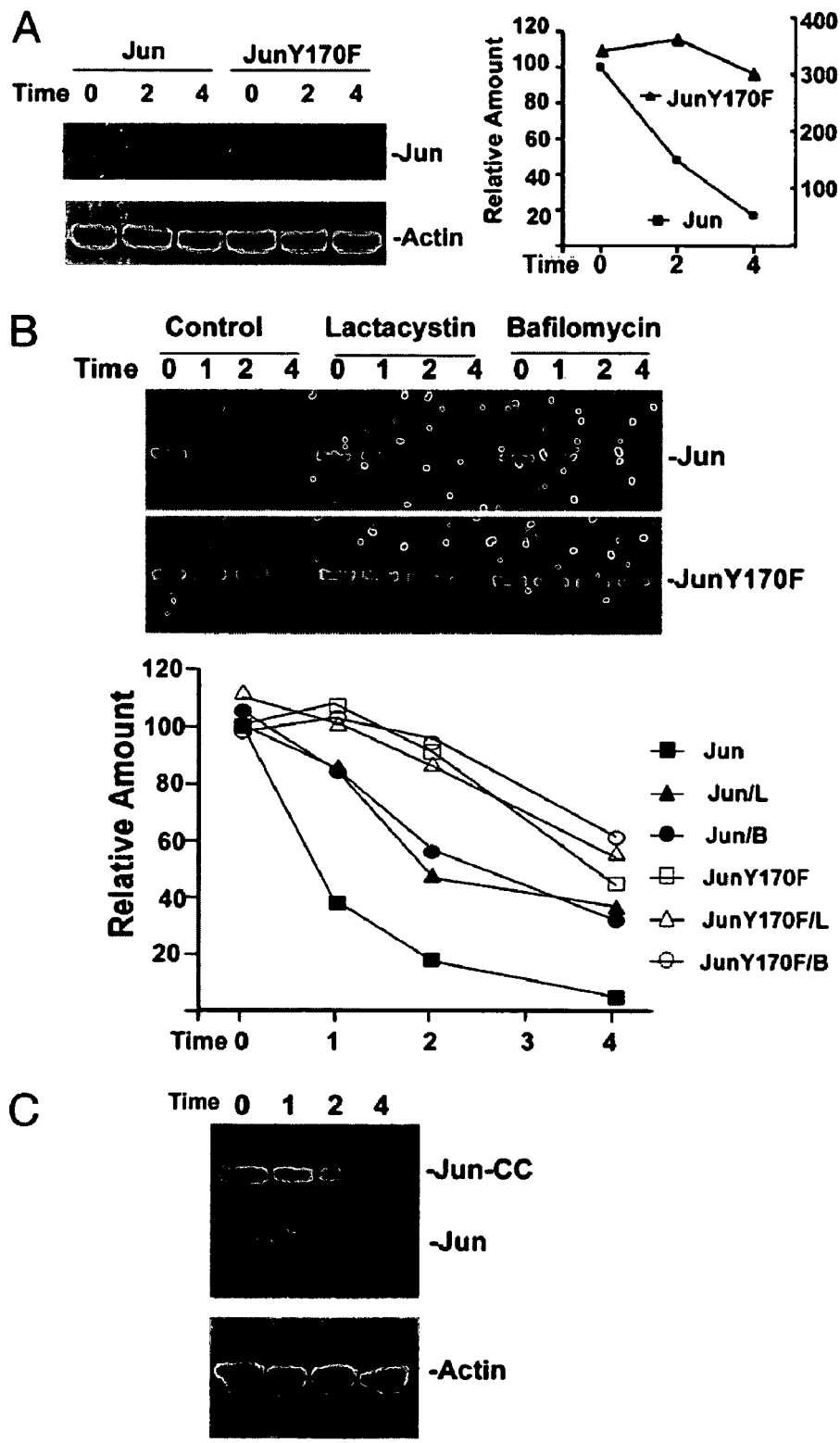
FIG. 6 shows stabilization of Jun by the Y170F mutation and by inhibitors of proteasomes and lysosomal $H^+$-ATPase. (A) Jun and JunY170F with Xpress epitope tags were expressed in HEK293T cells. (B) COS-1 cells that expressed Jun or JunY170F with Xpress epitope tags were labeled with $^{35}$S amino acids. (C) Jun-CC was expressed in COS-1 cells.

Degradation of Ubiquitinated Jun. To investigate the role of ubiquitination by Itch in Jun turnover, the effects of the Y170F mutation on the stability of Jun were examined. The steady-state level of JunY170F expression was higher than that observed for wildtype Jun when equal amounts of plasmids encoding the proteins were transfected into cells (FIG. 6A). When protein synthesis was blocked by the addition of cycloheximide, ≈50% of wild-type Jun was degraded in 1 h. Greater than 50% of JunY170F was degraded in 4 h (longer incubation caused morphological changes and cell death). To ascertain whether the difference between the levels of expression of wild-type and Y170F Jun was caused by a difference between their rates of degradation, their half-lives were measured by pulse-chase analysis (FIG. 6B). Wild-type Jun had a half-life of 1 h, whereas JunY170F has a half-life of 4 h. Thus, the Y170F mutation markedly stabilized Jun in transfected cells.

Because ubiquitinated Jun was localized to endolysosomal vesicles, and the Y170F mutation that eliminated Jun ubiquitination also reduced its rate of degradation, the role of lysosomes in Jun degradation was examined. Treatment of cells with chloroquine or bafilomycin A that inhibit lysosomal $H^+$-ATPase extended the half-life of Jun to 2 h (FIG. 6B). Treatment of cells with the MG132 or lactacystin proteosome inhibitors also increased the half-life of Jun to 2 h (FIG. 6B). None of these inhibitors affected the degradation of JunY170F. Thus, either the degradation of Jun involved both the proteasomal and lysosomal pathways, or these inhibitors had indirect effects on multiple pathways.

To examine whether transiently transfected Jun fused to a fluorescent protein fragment and epitope-tagged Jun were valid models for the study of Jun degradation, their half-lives were compared with that of endogenous Jun in the same cells. All of the proteins exhibited virtually identical rates of degradation (FIG. 6C). The average level of exogenous Jun in transfected cells was 6-fold higher than the level of endogenous Jun. This modest level of overexpression did not alter the rate of degradation, suggesting that the transiently expressed fusion proteins were degraded via the same pathway(s) as endogenous Jun.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method of detecting covalent modification of a protein, comprising:
   a) providing
      i) a first fusion protein comprising a first fragment of a fluorescent protein linked to ubiquitin, wherein said first fragment of a fluorescent protein is selected from the group consisting of SEQ ID NOs: 3, 5, 9, and 10; and
      ii) a second fusion protein comprising a second fragment of said fluorescent protein linked to said protein of interest, wherein said second fragment of a fluorescent protein is selected from the group consisting of SEQ ID NOs: 2, 4,6,7,8, and 11; and
   b) contacting said first and second fragments of said fluorescent protein under conditions such that said first and second fragments of said fluorescent protein re-associate to form a fluorescent protein that generates a optically detectable signal in the presence but not the absence of covalent modification of said protein of interest by said ubiquitin of said first fusion protein.

2. The method of claim 1, wherein said first and second fusion proteins are in a cell.

3. The method of claim 1, wherein said first fusion protein is encoded by a first vector comprising a first nucleic acid sequence encoding said first fragment of said fluorescent protein and a second nucleic acid sequence encoding said ubiquitin protein and said second fusion protein is encoded by a second vector comprising a third nucleic acid sequence encoding said second fragment of said fluorescent protein and a fourth nucleic acid encoding said protein of interest.

4. A method of screening compounds, comprising:
   a) providing
      i) a first fusion protein comprising a first fragment of a fluorescent protein linked to ubiquitin, wherein said first fragment of a fluorescent protein is selected from the group consisting of SEQ ID NOs: 3,5,9, and 10;

ii) a second fusion protein comprising a second fragment of said fluorescent protein linked to said protein of interest, wherein said protein of interest is known to be covalently modified by said ubiquitin protein, wherein said second fragment of a fluorescent protein is selected from the group consisting of SEQ ID NOs: 2, 4,5,7,8, and 11; and b) contacting said first and second fusion proteins and said test compound; and c) detecting the presence or absence of a fluorescent signal.

5. The method of claim 4, wherein fluorescence signal is altered relative to the fluorescence signal in the absence of said test compound.

6. The method of claim 5, wherein said fluorescent signal is decreased in the presence of said test compound.

7. The method of claim 4, wherein said first and second fusion proteins are in a cell.

8. The method of claim 4, wherein said first fusion protein is encoded by a first vector comprising a first nucleic acid sequence encoding said first fragment of said fluorescent protein and a second nucleic acid sequence encoding said ubiquitin protein and said second fusion protein is encoded by a second vector comprising a third nucleic acid sequence encoding said second fragment of said fluorescent protein and a fourth nucleic acid encoding said protein of interest.

* * * * *

UNITED STATES PATENT AND TRADEMARK OFFICE
CERTIFICATE OF CORRECTION

PATENT NO. : 7,588,907 B2
APPLICATION NO. : 11/445612
DATED : September 15, 2009
INVENTOR(S) : Tom Kerppola Page 1 of 1

It is certified that error appears in the above-identified patent and that said Letters Patent is hereby corrected as shown below:

Column 39, in between lines 9 and 10 please insert --iii) one or more test compounds; and--

Signed and Sealed this

Fifteenth Day of December, 2009

David J. Kappos
*Director of the United States Patent and Trademark Office*

```
                        SEQUENCE LISTING

<160> NUMBER OF SEQ ID NOS: 11

<210> SEQ ID NO 1
<211> LENGTH: 24
<212> TYPE: PRT
<213> ORGANISM: Artificial Sequence
<220> FEATURE:
<223> OTHER INFORMATION: Synthetic
<400> SEQUENCE: 1
Ala Asn Ser Ser Ile Asp Leu Ile Ser Val Pro Val Glu Tyr Pro Tyr
1               5                   10                  15

Asp Val Pro Asp Tyr Ala Ser Arg
            20

<210> SEQ ID NO 2
<211> LENGTH: 155
<212> TYPE: PRT
<213> ORGANISM: Artificial Sequence
<220> FEATURE:
<223> OTHER INFORMATION: Synthetic

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80
```

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala
145                 150                 155

<210> SEQ ID NO 3
<211> LENGTH: 84
<212> TYPE: PRT
<213> ORGANISM: Artificial Sequence
<220> FEATURE:
<223> OTHER INFORMATION: Synthetic

<400> SEQUENCE: 3

Asp Lys Gln Lys Asn Gly Ile Lys Val Asn Phe Lys Ile Arg His Asn
1               5                   10                  15

Ile Glu Asp Gly Ser Val Gln Leu Ala Asp His Tyr Gln Gln Asn Thr
            20                  25                  30

Pro Ile Gly Asp Gly Pro Val Leu Leu Pro Asp Asn His Tyr Leu Ser
        35                  40                  45

Tyr Gln Ser Ala Leu Ser Lys Asp Pro Asn Glu Lys Arg Asp His Met
    50                  55                  60

Val Leu Leu Glu Phe Val Thr Ala Ala Gly Ile Thr Leu Gly Met Asp
65                  70                  75                  80

Glu Leu Tyr Lys

<210> SEQ ID NO 4
<211> LENGTH: 173
<212> TYPE: PRT
<213> ORGANISM: Artificial Sequence
<220> FEATURE:
<223> OTHER INFORMATION: Synthetic

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140
```

-continued

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu
                165                 170

<210> SEQ ID NO 5
<211> LENGTH: 66
<212> TYPE: PRT
<213> ORGANISM: Artificial Sequence
<220> FEATURE:
<223> OTHER INFORMATION: Synthetic

<400> SEQUENCE: 5

Asp Gly Ser Val Gln Leu Ala Asp His Tyr Gln Gln Asn Thr Pro Ile
1               5                   10                  15

Gly Asp Gly Pro Val Leu Leu Pro Asp Asn His Tyr Leu Ser Tyr Gln
                20                  25                  30

Ser Ala Leu Ser Lys Asp Pro Asn Glu Lys Arg Asp His Met Val Leu
            35                  40                  45

Leu Glu Phe Val Thr Ala Ala Gly Ile Thr Leu Gly Met Asp Glu Leu
    50                  55                  60

Tyr Lys
65

<210> SEQ ID NO 6
<211> LENGTH: 173
<212> TYPE: PRT
<213> ORGANISM: Artificial Sequence
<220> FEATURE:
<223> OTHER INFORMATION: Synthetic

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu
                165                 170

<210> SEQ ID NO 7
<211> LENGTH: 173
<212> TYPE: PRT
```

```
<213> ORGANISM: Artificial Sequence
<220> FEATURE:
<223> OTHER INFORMATION: Synthetic

<400> SEQUENCE: 7

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu
                165                 170

<210> SEQ ID NO 8
<211> LENGTH: 173
<212> TYPE: PRT
<213> ORGANISM: Artificial Sequence
<220> FEATURE:
<223> OTHER INFORMATION: Synthetic

<400> SEQUENCE: 8

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

Gly Ile Lys Val Asn Phe Lys Ile Arg His Asn Ile Glu
            165                 170

<210> SEQ ID NO 9
<211> LENGTH: 156
<212> TYPE: PRT
<213> ORGANISM: Artificial Sequence
<220> FEATURE:
<223> OTHER INFORMATION: Synthetic

<400> SEQUENCE: 9

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp
145                 150                 155

<210> SEQ ID NO 10
<211> LENGTH: 273
<212> TYPE: PRT
<213> ORGANISM: Artificial Sequence
<220> FEATURE:
<223> OTHER INFORMATION: Synthetic

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

```
Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Ala Asn Ser
            165                 170                 175

Ser Ile Asp Leu Ile Ser Val Pro Val Glu Tyr Pro Tyr Asp Val Pro
            180                 185                 190

Asp Tyr Ala Ser Arg Met Gln Ile Phe Val Lys Thr Leu Thr Gly Lys
            195                 200                 205

Thr Ile Thr Leu Glu Val Glu Ser Ser Asp Thr Ile Asp Asn Val Lys
            210                 215                 220

Ser Lys Ile Gln Asp Lys Glu Gly Ile Pro Pro Asp Gln Gln Arg Leu
225                 230                 235                 240

Ile Phe Ala Gly Lys Gln Leu Glu Asp Gly Arg Thr Leu Ser Asp Tyr
            245                 250                 255

Asn Ile Gln Lys Glu Ser Thr Leu His Leu Val Leu Arg Leu Arg Gly
            260                 265                 270

Gly

<210> SEQ ID NO 11
<211> LENGTH: 85
<212> TYPE: PRT
<213> ORGANISM: Artificial Sequence
<220> FEATURE:
<223> OTHER INFORMATION: Synthetic

<400> SEQUENCE: 11

Ala Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
            35                  40                  45

Ser Tyr Gln Ser Ala Leu Ser Lys Asp Pro Asn Glu Lys Arg Asp His
    50                  55                  60

Met Val Leu Leu Glu Phe Val Thr Ala Ala Gly Ile Thr Leu Gly Met
65                  70                  75                  80

Asp Glu Leu Tyr Lys
                85
```